United States Patent [19]
Lambers et al.

[11] Patent Number: 6,001,375
[45] Date of Patent: Dec. 14, 1999

[54] TOPICAL APPLICATION OF CERAMIDES

[75] Inventors: Johannes Wilhelmus Jacobus Lambers, Pijnacker; Ernst-Ludwig Roehl, Naarden, both of Netherlands

[73] Assignee: Gist-brocades, B.V., Netherlands

[21] Appl. No.: 08/687,574

[22] PCT Filed: Nov. 28, 1995

[86] PCT No.: PCT/EP95/04714

§ 371 Date: Oct. 16, 1996

§ 102(e) Date: Oct. 16, 1996

[87] PCT Pub. No.: WO96/16635

PCT Pub. Date: Jun. 6, 1996

[30] Foreign Application Priority Data

Nov. 28, 1994 [EP] European Pat. Off. .............. 94203452
Apr. 27, 1995 [GB] United Kingdom .................... 9508604

[51] Int. Cl.[6] .................................................. A61K 7/48
[52] U.S. Cl. .......................... 424/401; 514/627; 514/629; 514/844; 514/847
[58] Field of Search ............................ 424/401; 514/627, 514/629, 844, 847

[56] References Cited

U.S. PATENT DOCUMENTS 5,476,661  12/1995  Pillai et al. ............................. 424/401
5,607,980  3/1997  McAtee et al. ......................... 514/476

OTHER PUBLICATIONS

Elias, P.M., "Epidermal Lipids, Barrier Function, and Desquamation" *J Invest Dermatol* (1983) 80:44–49.

Elias, P.M., et al., "Structural and Lipid Biochemical Correlates of the Epidermal Permeability Barrier" *Adv Lipid Res* (1991) 24:1–23.

Holleran, W.M., et al., "Processing of Epidermal Glucosylceramides is Required for Optimal Mammalian Cutaneous Permeability Barrier Function" *J Clin Invest* (1991) 91:1656–1664.

Kerscher, M., et al., "Skin Ceramides: Structure and Function" *Eur J Dermat* 1:39–43.

Wertz, P.W., et al., "The Composition of the Ceramides from Human Stratum Corneum and from Comedones" *J. Invest Dermatol* (1985) 84:410–412.

*Primary Examiner*—Jyothsna Venkat
*Attorney, Agent, or Firm*—Morrison & Foerster, LLP

[57] ABSTRACT

The present invention discloses the topical application of ceramides. The present invention provides specific cosmetic compositions comprising a ceramide and an agent to target said ceramide to the proper site of the skin. Specifically it is shown that the ceramide-containing compositions have a high capacity for recovering diminished water-retaining properties of preheated or damaged skin. Furthermore, the ceramide-containing compositions are shown to protect the skin again irritation.

7 Claims, 7 Drawing Sheets

TOPICAL APPLICATION OF CERAMIDES

This application is a 371 of PCT/EP95/04714 filed Nov. 28, 1995.

TECHNICAL FIELD

The present invention relates to the topical application of ceramides. Specifically, the present invention discloses specific ceramide-containing compositions which comprise agents to enhance the targeting of a ceramide to the proper site of the skin.

BACKGROUND OF THE INVENTION

Lipid lamellar structures in the intercellular spaces of the stratum corneum are considered to be responsible for the water retaining properties of the stratum corneum (Elias, P. M. (1983), J. Invest. Dermatol. 80, 44–49). It is generally understood that ceramides present within these intercellular lipid lamellae of the stratum corneum have an important structural function in the water impermeability barrier of the skin. The ceramides have shown to be essential in maintaining said barrier (Elias et al., (1991) Adv. Lipid Res. 24, 1–23).

Ceramides are a specific class of lipids belonging to the group of sphingolipids. A sphingolipid is a general term for all lipids containing sphingosine, phytosphingosine or sphinganine as a basic building block. Among the sphingolipids, the ceramides are the most abundant lipids present in the stratum corneum. In mammalian skin, seven predominantly occurring ceramides have been identified. These are mentioned ceramide 1, 2, 3, 4, 5, 6I and 6II (as defined in Wertz et al., (1985) J. Invest. Dermatol. 84, 410–412 and Kerscher et al. (1991), Eur. J. Dermat. 1, 39–43).

It is believed that one of the causes of dry skin is a reduction in the amount of ceramides within the intercellular lipid lamellae. It is therefore desirable to be able successfully to replace these depleted lipids via the topical route.

Ceramides must be able to penetrate the stratum corneum in order to reach the lipid lamellae of the permeability barrier. One of the unsolved problems with the topical application of skin products is to find a suitable way to deliver the active ingredient in sufficient amounts to the place where it must exert its biological activity.

Ceramides are extremely insoluble compounds, a property directly linked to their intrinsic functionality, i.e. the formation of a water-impermeable barrier. As a consequence they are not easy to formulate.

To circumvent these formulation problems, products have been introduced on the market which are not identical, but similar in structure to ceramides. Ceramide-like compounds which are commercially available to date mainly are glycosylceramides (cerebrosides), which are isolated from plant or animal sources, or pseudoceramides, which are no real ceramides but which have an ceramide-analogous structure.

In contrast to real ceramides, glycosylceramides have a relatively high solubility and are easy to formulate. However, it has for instance been shown that glycosylceramides do disturb skin barrier function rather than improving or restoring said function (Holleran et al. (1993) J. Clin. Invest. 91, 1656–1664). Also pseudoceramides, synthetic ceramide-like compounds, often have a higher solubility as compared to ceramides, but these have the disadvantage that they are not biodegradable and consequently can easily accumulate in the skin.

The development of specific formulations which are able to target ceramides to the proper site of the skin is of crucial importance to guarantee efficacy of ceramides.

SUMMARY OF THE INVENTION

The present invention provides ceramide-containing compositions for topical use. The compositions are characterized in that they contain a ceramide and a skin penetration enhancer to target said ceramide to the proper site of the skin, i.e. the stratum corneum.

The skin penetration enhancer preferably is a nonionic or an anionic surfactant.

The nonionic surfactant preferably is an alkoxylated surfactant, more preferably an ethoxylated surfactant. Most preferably, the skin penetration enhancer is selected from the group comprising Ceteareth-2 to Ceteareth-100.

The anionic surfactant preferably is selected from the group of fatty acids or fatty acid derivatives containing one or more carboxylic groups to be neutralized by means of an alkali metal, like K, Na, Ca, Mg, Al, or an organic alkaline substance, like triethanol amine, such as alkali soaps of fatty acids. More preferably, the anionic surfactant is selected from the group of sodium, potassium, triethanol amine stearates, isostearates and oleates.

The composition of the present invention additionally may comprise a polyglyceryl ester as a solubilizing agent.

The present invention preferably discloses ceramide-containing compositions, in which the ceramide component is an individual ceramide in a pure form or a mixture of two or more individual ceramides. A preferred ceramide is selected from the group of ceramide 1, 2, 3, 4, 5, 6I and 6II. Another preferred ceramide is selected from the group of N-tetracosanoyl phytosphingosine, N-stearoyl phytosphingosine, N-oleoyl phytosphingosine, N-linoleoyl-phytosphingosine, N-(2-hydroxytetracosanoyl) phytosphingosine, N-(2-hydroxyoctadecanoyl) phytosphingosine, N-(27-stearoyloxyheptacosanoyl) phytosphingosine, N-(27-oleoyloxyheptacosanoyl) phytosphingosine, N-(27-linoleoyloxyheptacosanoyl) phytosphingosine, N-(23-stearoyloxytricosanoyl) phytosphingosine.

Topical application of the compositions of the present invention on pretreated skin shows a high capacity of the ceramides for improvement of the water-retaining capacity of the skin, for restoration of a damaged skin lipid barrier and for protection of the skin against surfactant-induced irritation, i.e. protection of the lipid barrier against damaging influences.

DETAILED DESCRIPTION OF THE INVENTION

Figure 1:
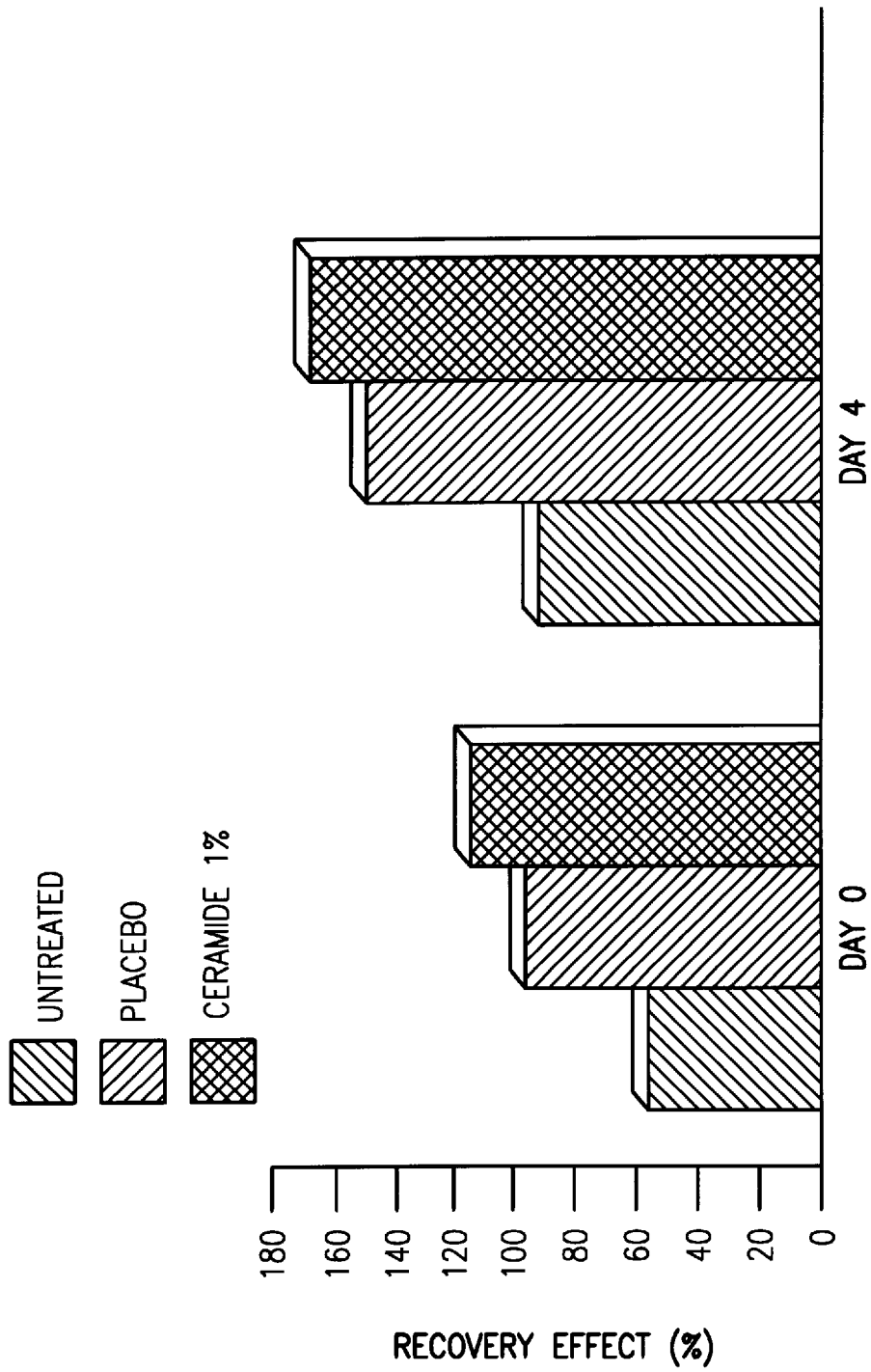
FIG. 1 shows the recovery effect of Ceramide III on the skin after aceton/ether treatment, as measured by corneometry.

The present invention discloses ceramide-containing compositions for topical application. Specific ceramide-containing compositions are disclosed comprising agents which ensure targeting of the ceramide to the proper site of the skin, i.e. the stratum corneum. Consequently, high efficacy of the ceramides is ensured.

The compositions of the present invention contain specific compounds that are able to interact with the stratum corneum to alter its natural resistance. These compounds are called penetration enhancers.

Various compounds can display a function as penetration enhancer, e.g. solvents and amphiphilic (surface active) compounds.

The skin penetration enhancers which are present in the compositions of the present invention preferably are selected from the group of surface active compounds. More preferably they are alkoxylated surfactants, most preferably ethoxylated surfactants such as fatty alcohol and fatty acid ethoxylates or mixtures thereof. Especially preferably, the ethoxylated surfactants are selected from the group comprising Ceteareth-2 to Ceteareth-100.

Another preferred group of surface active compounds is the group of anionic surfactants. An anionic surfactant can be selected from the group of soaps, N-acylamino acid salts, alkylethercarboxylates, alkylphosphates, alkyletherphosphates, N-acyltaurates and alkyllactylates. Preferably, the anionic surfactant is a fatty acid or fatty acid derivative containing one or more carboxylic groups to be neutralized by means of an alkali metal, like K, Na, Ca, Mg, Al, or an organic alkaline substance, like triethanol amine. Most preferably, the anionic surfactant is selected from the group of alkali soaps of fatty acids, most preferably sodium, potassium, triethanol amine stearates, isostearates and oleates.

The skin penetration enhancers can be used in a concentration ranging from 0.1% to 30%, preferably from 0.5% to 15%, more preferably from 1% to 10%, most preferably from 3 to 5% by weight of the composition.

The skin penetration enhancers further may be used in combination with an oil, more preferably a vegetable oil, most preferably avocado oil.

The compositions of the present invention additionally may include a solubilizing agent, such as a polyglyceryl ester. The polyglyceryl ester preferably is selected from the group comprising decaglyceryl tri-, decaglyceryl penta- and decaglyceryl heptaisostearate. Another preferred polyglycerylester is selected from the group comprising di-, tri- and tetra glyceryl caprate and di-, tri- and tetra glyceryl caprylate.

It was observed that the compositions of the present invention advantageously do not contain crystals. The presence of crystals in the composition is undesirable, since crystals will diminish the performance of the composition regarding targeting of a ceramide to the proper site of the skin. In other words, the presence of crystals will diminish the penetration enhancing ability of the composition.

The ceramides which are present in the compositions of the invention are understood to have a structure which is comparable to that of the ceramides identified as ceramide 1, 2, 3, 4, 5, 6I and 6II. More specifically, the ceramides which are present in the compositions of the invention are understood to comprise ceramides in which the sphingoid base backbone is selected from the group of sphingosine, phytosphingosine and sphinganine, wherein said sphingoid base backbone is acylated with an acyl or an acyloxyacyl group, wherein said acyl or acyloxyacyl group can have a variable chain length, optionally can have (additional) double bonds, optionally can contain a hydroxyl group and optionally can be branched.

The compositions of the present invention preferably contain a ceramide in a pure form, i.e. without the presence of other sphingolipid compounds. Wherein pure is defined as more than 50% pure, preferably more than 80% pure. It is also envisaged by the present invention to employ mixtures of individual ceramides. The availability of individual ceramides in a pure form enables the use of specific optimized ratios of the individual ceramides.

To obtain ceramides in a pure form, several methods are available to the skilled person, including:
  chemical synthesis. This is difficult in view of the required stereochemistry.
  enzymatical synthesis.
  chemical conversion of glycosylceramides and/or sphingomyelins isolated and purified from crude extracts of animal or plant sources.
  acylation of fermentation derived (phyto)sphingosines.

Especially the latter method yields pure ceramides in high amounts.

The acylation of (phyto)sphingosine can be performed in an efficient way by using for example the selective acylation method as disclosed in International Patent Application WO93/20038.

The compositions of the invention preferably contain a ceramide which is selected from the group of ceramide 1, 2, 3, 4, 5, 6I and 6II. Another preferred ceramide is selected from the group of N-tetracosanoyl phytosphingosine, N-stearoyl phytosphingosine, N-oleoyl phytosphingosine, N-linoleoyl-phytosphingosine, N-(2-hydroxytetracosanoyl) phytosphingosine, N-(2-hydroxyoctadecanoyl) phytosphingosine, N-(27-stearoyloxyheptacosanoyl) phytosphingosine, N-(27-oleoyloxyheptacosanoyl) phytosphingosine, N-(27-linoleoyloxyheptacosanoyl) phytosphingosine, N-(23-stearoyloxytricosanoyl) phytosphingosine.

Furthermore, the compositions of the present invention can also advantageously be used for the formulation of those pseudoceramides which are relatively difficult to solubilize.

The specific compositions of the present invention further include the usual components. The composition comprises a vehicle to enable the active ingredient to be conveyed to the skin. Vehicles include water, solids and liquids. These are classified as emollients, propellants, solvents, humectants, thickeners and powders.

Emollients include alkyl higher fatty acids, natural oils, higher fatty alcohols, glyceryl and isopropyl esters, mineral oils, silicones and fatty alcohol esters.

Propellants include propane, butane, isobutane, dimethyl ether, chlorofluoroalkanes, carbon dioxide, nitrous oxide.

Solvents include ethyl alcohol, methylene chloride, isopropanol, ethyl ethers, DMSO, propylene glycol, butylene glycol.

Humectants include proteins and protein hydrolysates, amino acids and polyols such as glycerin, sorbitol.

Thickeners include polysaccharides, gums and carboxylic group-containing polymers.

Powders include chalk, talc, starch.

The combination of the said components can account for 10 to 99% of the composition.

The compositions of the present invention are suitable for topical use. The amount of ceramide or mixture thereof suitable for topical application ranges from 0.001% to 25%, preferably from 0.005% to 5%, most preferably from 0.01 to 2% by weight of the composition.

By topical application of the ceramide-containing compositions of the present invention on pretreated or damaged skin, it is shown that the ceramides are highly effective. In particular, they have a high capacity for recovering diminished water-retaining properties of the skin, especially after damaging the skin. On healthy skin, ceramide compositions produce a clear moisturizing effect. In addition, pretreatment of the skin with the ceramide-containing compositions of the invention shows a clear protecting effect of ceramides against SDS-induced skin damage.

The present invention is illustrated by topical application of compositions containing the ceramides N-octadecanoyl-phytosphingosine (Ceramide III) and N-(2-hydroxyoctadecanoyl)-phytosphingosine (Ceramide VI).

Example 1 describes the effect of topical application of Ceramide III on skin pretreated with acetone/ether.

Example 2 describes several crystal-free ceramide formulations comprising either a nonionic or an anionic surfactant.

Examples 3 to 5 describe the application of compositions containing a nonionic surfactant and Ceramide III or Ceramide VI.

Example 6 describe the application of Ceramide III formulations comprising an anionic surfactant.

EXPERIMENTAL

Measurement Equipment

Skin Humidity

The corneometer CM 820 PC (Courage and Khazaka, Cologne, Germany) registers the electrical capacitance of the skin surface, which is a measure of the degree of moisture on the skin's surface. The capacitance is expressed digitally in arbitrary units (a.u.). Three measurements were performed on each test area and the mean was used to define hydration state of the stratum corneum.

The corneometer comprises a console and its sensor. The sensor is connected to the console by a special plug and coiled cable. The measurement is indicated on the 40×18 mm display screen on the console as a three-place number. The display also fulfils other information functions.

The sensor is rectangular in shape. Its special glass coated active front surface can be moved axially, and has a stroke of at least 3 mm. The measuring principle demands that the sensor surface be placed flat on the test object at a constant pressure. In order to ensure this as reproducibly as possible, the front surface of the measuring head has been designed to be very small (7×7 mm). The inner moveable part—the active front surface—is pressed against the skin by a spring using a force of 3.5 N.

The corneometer is completely automatic in operation. In order to carry out a measurement, the measuring head is pressed against the area of skin to be measured. The measured value is displayed after one second.

Roughness

Roughness was measured by profilometry using a stylus instrument (OFR 01; Romano GmbH, Cologne, Germany). Silicon impressions from the test areas of the volar forearm were prepared. The dental mass Silasoft N® (Detax-K. Huber K. G., Karlsruhe, Germany) was used for making the impressions. The parameter mean depth of roughness $R_z$ (DIN 4768/1) was measured. By convention the scan length was divided into three equal-sized areas. In each area the distance from the highest peak to the lowest trough was established. The average of these five distances is $R_z$.

Trans-epidermal water loss

Measurements of trans-epidermal water loss (TEWL) were performed with the Tewameter (Courage & Khazaka, Cologne, Germany). The Tewameter is a device for measurement of water evaporation on skin surfaces based on the diffusion principle discovered by A. Fick in 1885.

Skin colour

Skin colour was measured by chromametry with a Minolta Chromameter CR 300 (Minolta, Ahrensburg, Germany) in compliance with the Commission International de l'eclairage (CIE) system, according to which the registration of colour is adjusted to the non-linear colour sensitivity of human eye. A colour is expressed in a three-dimensional coordinate system with green-red (a*), yellow-blue (b*) and L* axes (brightness). The skin surface is illuminated by a Xenon flash light and remitted light registered and analysed by a photoreceiver. Chromametry is sensitive and accurate for the characterization of redness of skin irritation. In inflamed skin a positive change on the a* axis is observed, towards red. Each value was the average of three recordings.

EXAMPLE 1

Application of Ceramide III

Test method 20 female volunteers at the age of 18 to 65 years with intact barrier function were included in the test. After a resting period of 30 minutes in a climatized chamber of 22° C. and 60% of relative humidity the test was carried out. All measurements were done in the climated chamber after at least 30 minutes of climatization.

Test design

| Day | Procedure | Application | Measurement |
|---|---|---|---|
| 0 | 1/1 Acetone/Ether 30 minutes | after Acetone/Ether extraction and measurement in the morning | before and directly after extraction, 6 h after first application |
| 1 | — | home application in the morning | — |
| 2 | — | home application in the morning | — |
| 3 | — | home application in the morning | — |
| 4 | — | home application in the morning | 6 h after last application on day 4 |

The test was carried out on the volar forearm. To extract the skin, glass cylinders were fixed on the skin and 10 ml of Acetone/Ether (1/1 v/v) were filled into the cylinders for 30 minutes. The extraction was carried out simultaneously on 4 test areas on the volar forearms. Directly before and after extraction corneometer measurements were carried out in each test area. Each time 8 single values were taken and averaged on each test area.

After measuring the test products were applied, one area remained untreated. The dose of application was 2 mg/cm². Five hours and 30 minutes after the first application the volunteers were climatized again for 30 minutes and the corneometer measurements were repeated. In the following three days a home application in the morning took place. The volunteers applied the test products using preweighted syringes to obtain the amount of 2 mg/cm². In the morning of day 4 the test products were applied again and the last measurement was carried out 6 hours after this application. Formulations tested

| Raw Material | Concentration | CTPA | Supplier |
|---|---|---|---|
| Eumulgin B3 | 13.0 | Ceteareth-30 | Henkel, Düsseldorf |
| Cetiol HE | 20.0 | PEG-7-Glyceryl Cocoate | Henkel, Düsseldorf |
| Paraffin perliquidum | 2.7 | Mineral Oil | Wagner, Lüneburg |
| Water | ad 100 | | |
| Ceramide III | 0 (placebo) 1.0 | | |

Results are shown in FIG. 1. Each value is an average of 8 measurements. Mean and standard deviation are calculated. Measurements are expressed as the percental change of the values as compared to untreated areas. The measurements were standardized to the individual baseline, which was taken before delipidation.

Ceramide III 1% shows a significant difference (p<0,05) compared to placebo on day 0, 6 h after the first application and a strong tendency (p<0,1) on day 4, 6 h after last application.

6 hours after the first application the ceramide containing formulation shows a 50% better performance than the placebo realtive to the untreated areas; even after 4 days, 6 hours after the last application the improvement of the water content in the stratum corneum is 27%.

TABLE 1

O/W-emulsions with Ceramide III

| | anionic | | | nonionic | | |
|---|---|---|---|---|---|---|
| Component | 1 | 2 | 3 | 4 | 5 | 6 |
| Ceteareth-6 (and) stearyl alcohol | — | — | — | 3.25 | 3.25 | 3.25 |
| Ceteareth-25 | — | — | — | 1.75 | 1.75 | 1.75 |
| Glyceryl stearate SE | 5.00 | 5.00 | 5.00 | — | — | — |
| Caprylic/capric triglyceride | 3.00 | 3.00 | 3.00 | 3.00 | 3.00 | 3.00 |
| Stearyl Beeswaxate | 1.00 | 1.00 | 1.00 | 1.00 | 1.00 | 1.00 |
| Decaglyceryl pentaisostearate (PG-5IS) | — | 5.00 | — | — | 5.00 | — |
| Polyglyceryl tri-caprylate/tricaprate (1010S TC) | — | — | 5.00 | — | — | 5.00 |
| Cetyl alcohol | 2.50 | 2.50 | 2.50 | 2.50 | 2.50 | 2.50 |
| Avocado Oil | 5.00 | 5.00 | 5.00 | 5.00 | 5.00 | 5.00 |
| Octyl stearate | 2.00 | 2.00 | 2.00 | 2.00 | 2.00 | 2.00 |
| Dioctylcyclohexane | 3.00 | 3.00 | 3.00 | 3.00 | 3.00 | 3.00 |
| Ceramide III | 0/0.50 | 0/0.50 | 0.50 | 0/0.50 | 0/0.20/ 0.50 | 0.50 |
| Preservative* | 0.50 | 0.50 | 0.50 | 0.50 | 0.50 | 0.50 |
| Water | ad. 100 | ad. 100 | ad. 100 | ad. 100 | ad. 100 | ad. 100 |

*Propylene glycol (and) phenoxyethanol (and) methylparaben (and) propylparaben (and) ethylparaben (and) butylparaben

EXAMPLE 2

Crystal-Free Ceramide Formulations

Two type of formulations have been developed for topical application of ceramides, which differ in the surfactant which is used. One type comprises an nonionic surfactant, the other an anionic surfactant. Some different nonionic and anionic formulations are depicted in Table 1. All formulations were shown to be free of crystals, a property which is important to obtain maximal efficacy of ceramides.

EXAMPLE 3

Effect of Ceramide III in a Nonionic Formulation on SDS-Damaged Skin

Formulations tested
    See Example 2, number 5.
Time of Evaluation
    after damaging the skin with SDS
    1 hour after last application on days 3, 7, 14
Test method Fifteen female volunteers at the age of 22–43 years with healthy skin were included in the test.

Measurements were carried out at a temperature of 22±1° C. and a relative humidity of 60±10%. Subjects were accustomed to ambient conditions for 20 min prior to any measurement. The test was carried out on the volar forearms. The skin of the forearms was treated with a 5% aqueous solution of sodium lauryl sulphate (SDS) and an occlusive dressing applied. The dressing was removed 2 h later, and the regions gently washed with water and air-dried. After 30 min the measurements were done. Then the three test products were applied, one area remained untreated. The dose of application was about 2 mg/cm$^2$. In the following 14 days a home application in the morning and evening took place.

Measurements were evaluated during the treatment period on day 3, 7 and 14 one hour after the last daily application. Use of other cosmetic products was restricted on the test areas throughout the whole study.

Results

Moisturing effect

Summary statistics (Statgraphics Plus Version 6, Manugistics U.S.A.) procedure was used to determine the center, spread, and shape of the data. The system performs the following calculations: average, median, variance, standard deviation, standard error, minimum and maximum.

Figure 2:
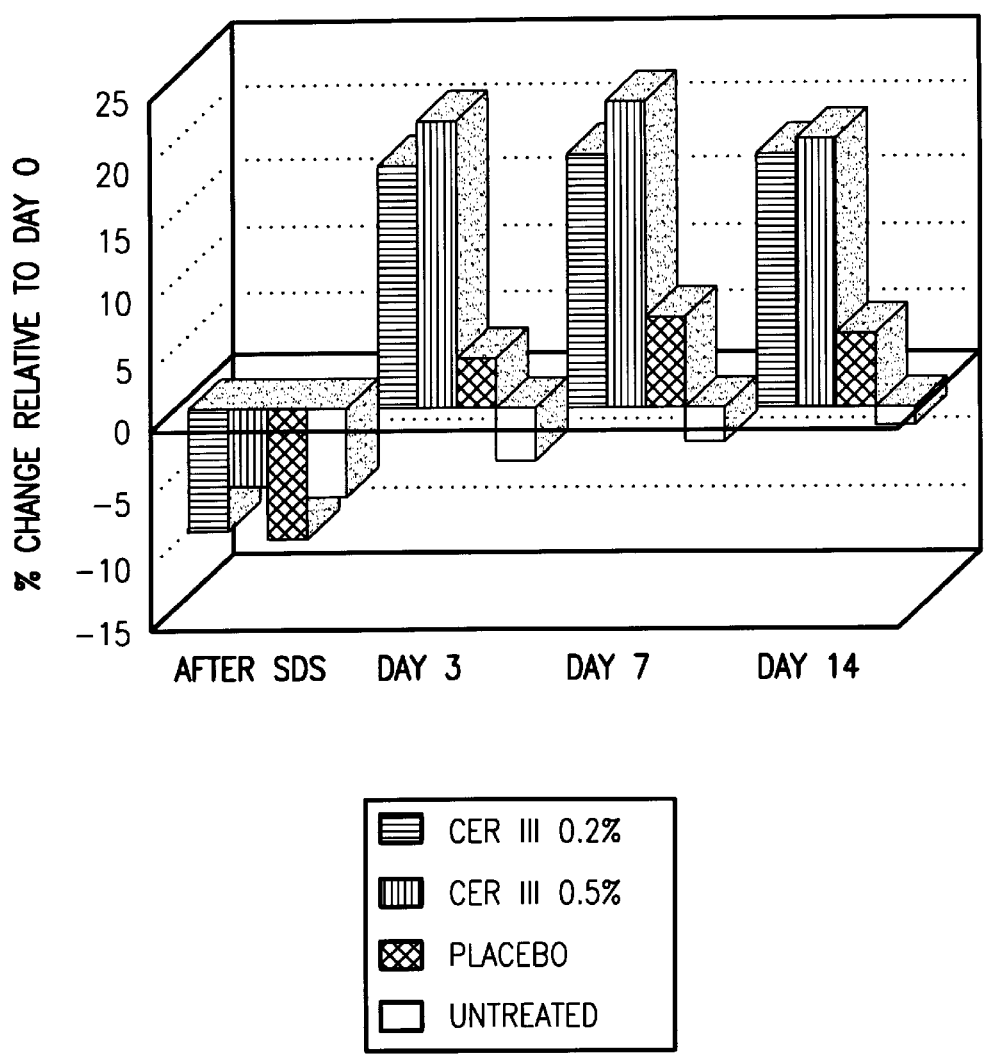
FIG. 2 shows the results of corneometer measurements on SDS-damaged skin, treated with a nonionic ceramide III formulation and placebo.

In FIG. 2 the results are depicted as a percentage change relative to day 0. The ceramide containing creams (0.2%, 0.5%) gave clear effects compared to placebo. With two daily applications the maximal effect was achieved after around 7 days.

Smoothening effect

Figure 3:
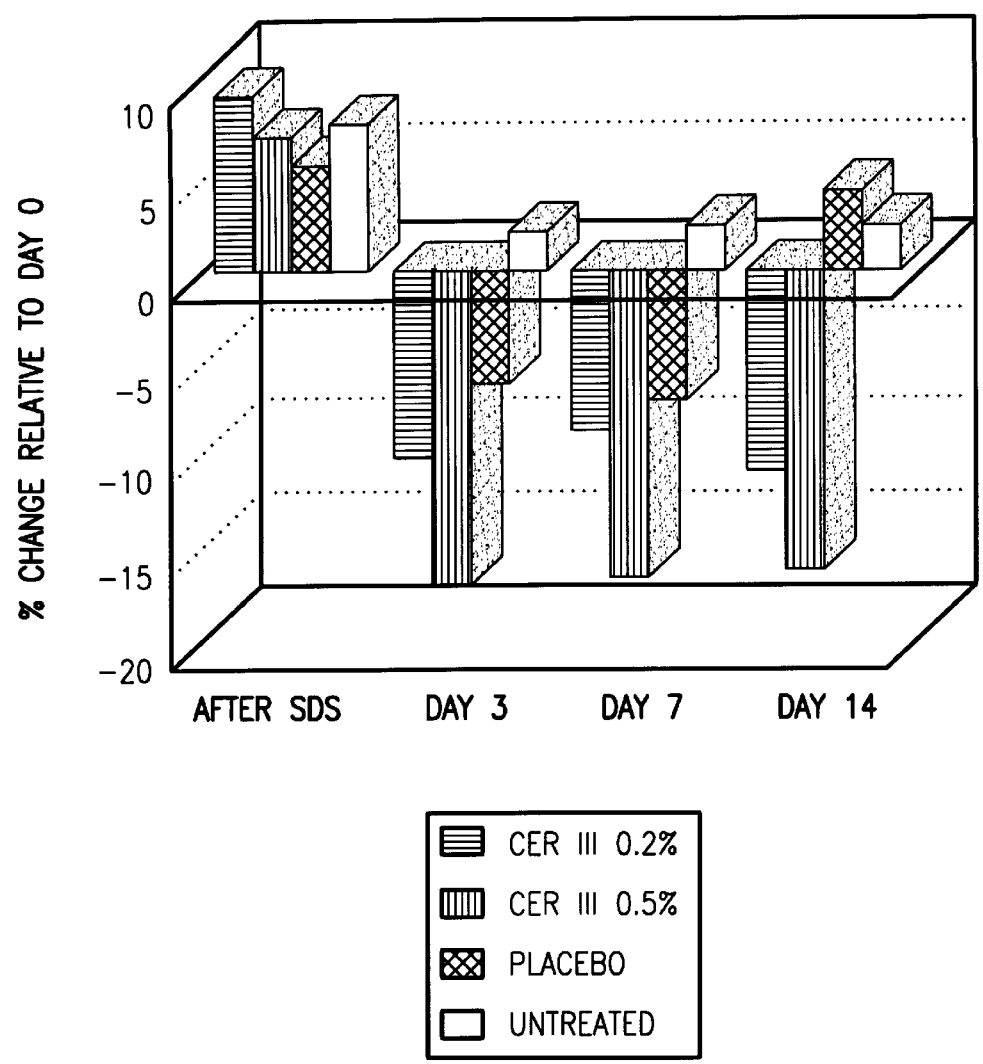
FIG. 3 shows the results of roughness measurements on SDS-damaged skin, treated with a nonionic ceramide III formulation and placebo.

FIG. 3 shows the results as a percentage change relative to day 0. The ceramide containing products decrease the roughness compared to placebo.

TEWL

Figure 4:
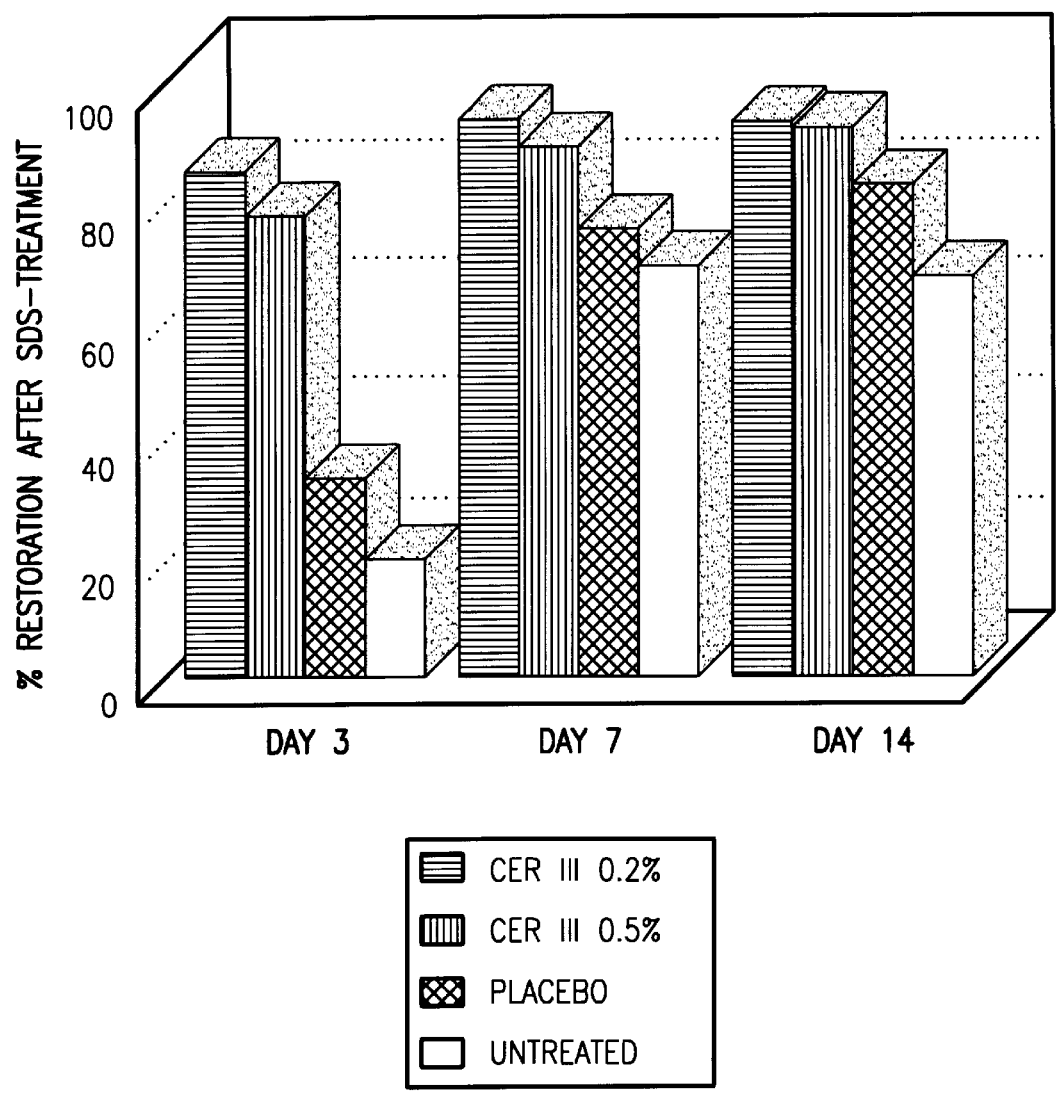
FIG. 4 shows the results of TEWL measurements on SDS-damaged skin, treated with a nonionic ceramide III formulation and placebo.

FIG. 4 shows the results expressed as percentage restoration after SDS-treatment. The ceramide containing products normalize the TEWL in a shorter time (only three days) than the placebo product (nearly 14 days). The TEWL in the untreated area takes more than 14 days to return to normality.

Conclusion

A treatment period of 14 days with the ceramide containing creams produced a reduction in skin roughness and a reduction of TEWL, accompanied with an increase of skin humidity of damaged skin compared to placebo.

Thus, the ceramide containing preparations lead to a quicker restitution of the barrier layer of SDS-damaged skin than the placebo product.

EXAMPLE 4

Long-Term Effects of Ceramide III in a Nonionic Formulation on Healthy Skin

Formulations tested

See Example 2, number 5.

Time of evaluation before treatment 2 hours after last application on days 7, 14, 28 four days after application was ceased

Test method

Fifteen female volunteers at the age of 28–40 years with healthy skin were included in the test.

Measurements were carried out at a temperature of 22±1° C. and a relative humidity of 60±10%. Subjects were accustomed to ambient conditions for 20 min prior to any measurement. The test was carried out on the volar forearms. Initially untreated skin was measured in all three areas to find baseline values. After measuring the three test products were applied, one area remained untreated. The dose of application was about 2 mg/cm$^2$. In the following 28 days a home application in the morning and evening took place.

Measurements were evaluated during the treatment period on day 7, 14 and 28 two hours after the last daily application. The application was ceased on day 28 and further measurements were evaluated on day 30 and 32. Use of other cosmetic products was restricted on the test areas throughout the whole study.

Results

Moisturing effect

Figure 5:
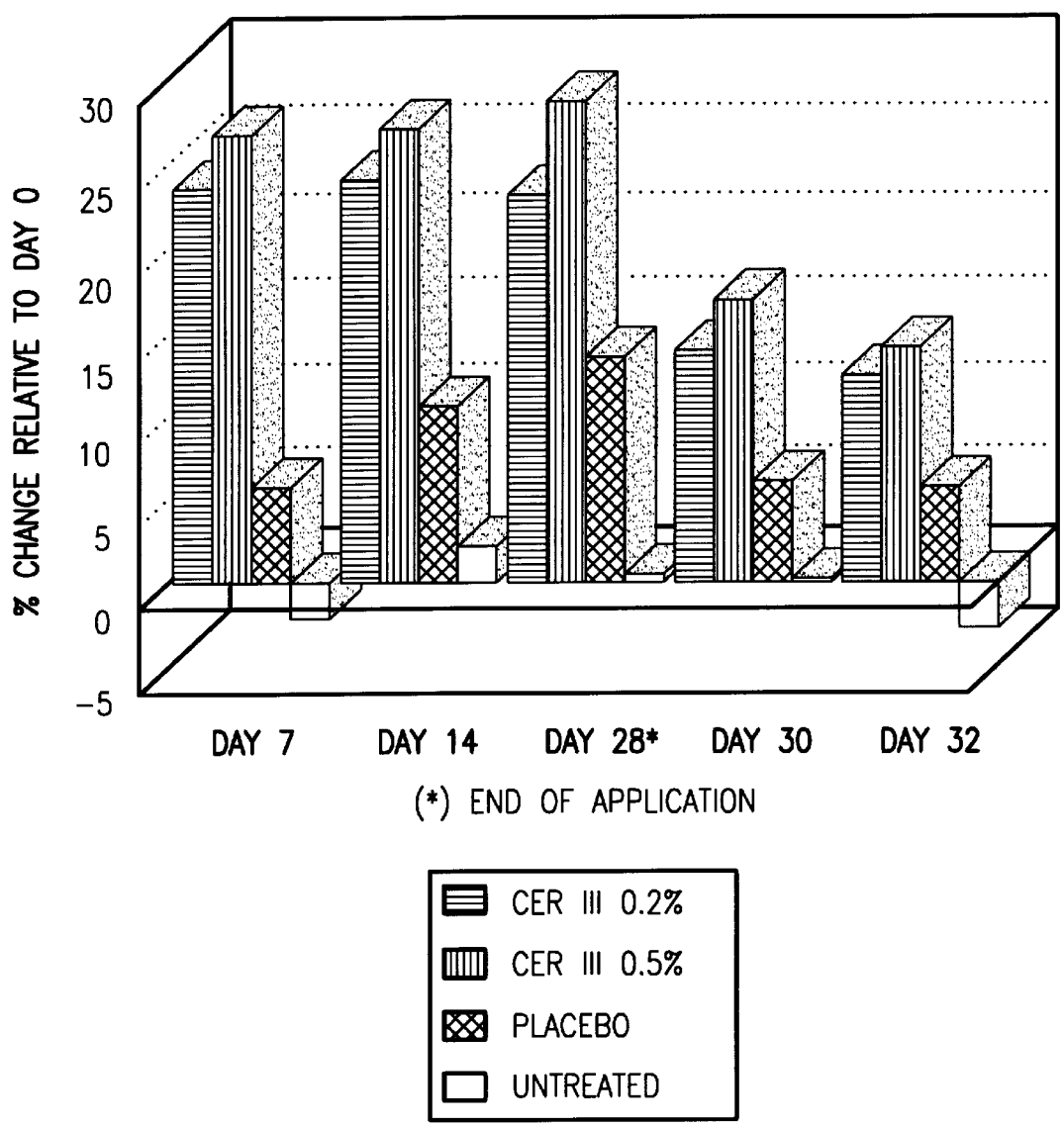
FIG. 5 shows the results of corneometer measurements on healthy skin, treated with a nonionic ceramide III formulation and placebo.

Summary statistics (Statgraphics Plus Version 6, Manugistics U.S.A.) procedure was used to determine the center, spread, and shape of the data. The system performs the following calculations: average, median, variance, standard deviation, standard error, minimum and maximum. FIG. 5 shows the mean results expressed as percentage change relative to day 0. The ceramide containing creams (0.2%, 0.5%) gave clear effects compared to placebo. With two daily applications the maximal effect was achieved after around 14 days and then remained nearly constant throughout the further application period. Two and four days after the last application the humidity of the skin was still significantly increased compared to placebo and untreated area.

Conclusion

The ceramide containing products gave clear moisturizing effects compared to placebo.

Thus, the effect of ceramide containing preparations in enhancing the properties of the stratum corneum with respect to its water retaining function is proved in this example.

EXAMPLE 5

Smoothening Effect of Ceramide VI in a Nonionic Formulation on Healthy Human Skin Formulations tested See Example 2, number 5. The formulations contain 0.05%, 0.2% and 0.5% Ceramide VI.

Time of evaluation before start of treatment;

two hours after last application on day 7;

2 hours after irritation with SDS (2 h under occlusion).

Test method

Two panels of each five female volunteers at the age of 19–55 years with healthy skin were included in the test. The participants were briefed on the study procedures and each gave written informed consent.

Measurements were carried out at a temperature of 22±1° C. and a relative humidity of 60±10%. Subjects were accustomed to ambient conditions for 20 min prior to any measurement. The test was carried out on the volar forearms. Initially untreated skin was measured in all six areas to find baseline values. Then the five test products were applied, one area remained untreated. The dose of applicaton was about 2 mg/cm$^2$. In the following 7 days a home application in the morning and evening took place. Measurements were evaluated during the treatment period on day 7 two hours after the last daily application. Then the test areas on both forearms were treated with a 5% aqueous solution of sodium lauryl sulphate (SDS) and an occlusive dressing applied to induce skin irritation. The dressing was removed 2 h later, and the regions were gently washed with water and air-dried. After 1 hour the measurements were done when the level had stabilised.

Use of other cosmetic products was restricted on the test areas throughout the whole study.

Results

The results of skin roughness measurements are indicated in Table 1. The values measured on day 7 and after SDS treatment should be compared to the corresponding starting value of day 0.

A decrease in roughness, much higher than the placebo, was found after 7 days in the areas treated with the formulations containing ceramide VI. After irritation with SDS, the roughness increased in the untreated area and in the area pretreated with placebo. only minimal changes were detected in the areas pretreated with the ceramide containing formulations.

TABLE 1

| | Results of skin roughness measurements | | | | |
|---|---|---|---|---|---|
| | 0.05% | 0.2% | 0.5% | Placebo | Untreated |
| day 0 | 113.9 ± 9.2 | 132.8 ± 11.3 | 135.6 ± 12.1 | 114.4 ± 8.7 | 101 ± 9.8 |
| after 7 days | 101.7 ± 10 | 106.8 ± 12.6 | 104.2 ± 10.4 | 106.7 ± 10.6 | 98.2 ± 10.4 |
| after SDS | 89.9 ± 2.4 | 108.7 ± 6 | 97.5 ± 17.6 | 119 ± 12.3 | 119.3 ± 14 |

EXAMPLE 6

Role of Ceramide VI in Preventing Surfactant-Induced Irritation of the Skin

See Example 5 for test method, formulations tested and time of evaluation.

Results

The results of TEWL and skin colour measurements are presented in respectively Table 2 and Table 3. The values measured on day 7 and after SDS treatment should be compared to the corresponding starting value of day 0.

After irritation with SDS, the increase of the TEWL in the areas pretreated with ceramide VI for 7 days was much lower compared to control and placebo pretreatment. The effect was dose dependent. A similar phenomenon could be observed using skin colour as a parameter. This shows that pretreatment with ceramide VI protects the skin from SDS-damage.

TABLE 2

Results of TEWL measurements

|  | 0.05% | 0.2% | 0.5% | Placebo | Untreated |
|---|---|---|---|---|---|
| day 0 | 5.2 ± 0.9 | 7.6 ± 1.3 | 5.2 ± 0.8 | 5.8 ± 1.5 | 5.5 ± 0.5 |
| after 7 days | 7.9 ± 3.9 | 7.5 ± 1 | 5.7 ± 1.5 | 5.4 ± 2.5 | 4.6 ± 2 |
| after SDS | 16.6 ± 6.3 | 11.7 ± 2.9 | 8.2 ± 3.1 | 18.1 ± 4.6 | 22 ± 7.7 |

TABLE 3

Results of skin colour measurements

|  | 0.05% | 0.2% | 0.5% | Placebo | Untreated |
|---|---|---|---|---|---|
| day 0 | 6.9 ± 0.9 | 6.7 ± 1.6 | 7.4 ± 1.3 | 6.9 ± 2.2 | 6.5 ± 1.7 |
| after 7 days | 7.3 ± 0.7 | 6.8 ± 0.8 | 6.9 ± 1.1 | 6.3 ± 1.1 | 6.6 ± 1.7 |
| after SDS | 14.2 ± 2.1 | 8.3 ± 0.8 | 7.3 ± 1.5 | 13.5 ± 0.7 | 16.9 ± 2.7 |

EXAMPLE 7

Long-Term Effects of Ceramide III in an Anionic Formulation on Healthy Skin

Formulations tested

See Example 2, numbers 1 and 2.

Time of evaluation before treatment 2, 4, 8 and 12 hours after first application 2 hours after last application on day 1, 3, 7 (stop of treatment), 8, 10, 13

Test method

Ten female volunteers with healthy skin were included in the test.

Measurements were carried out at a temperature of 22±1° C. and a relative humidity of 60±10%. Subjects were accustomed to ambient conditions for 20 min prior to any measurement. The test was carried out on the back leg. Initially untreated skin was measured in all three areas to find baseline values. After measuring the test products were applied, one area remained untreated. The dose of application was about 2 mg/cm$^2$. From day 1 through day 7, a home application in the morning and evening took place.

Measurements were evaluated 2, 4, 8 and 12 hours after first application and during the treatment period on day 1, 3 and 7, two hours after the last daily application. The application was ceased on day 7 and further measurements were evaluated on day 8, 10 and 13. Use of other cosmetic products was restricted on the test areas throughout the whole study.

Results

Moisturing effect

Summary statistics (Statgraphics Plus Version 6, Manugistics U.S.A.) procedure was used to determine the center, spread, and shape of the data. The system performs the following calculations: average, median, variance, standard deviation, standard error, minimum and maximum.

Figure 6:
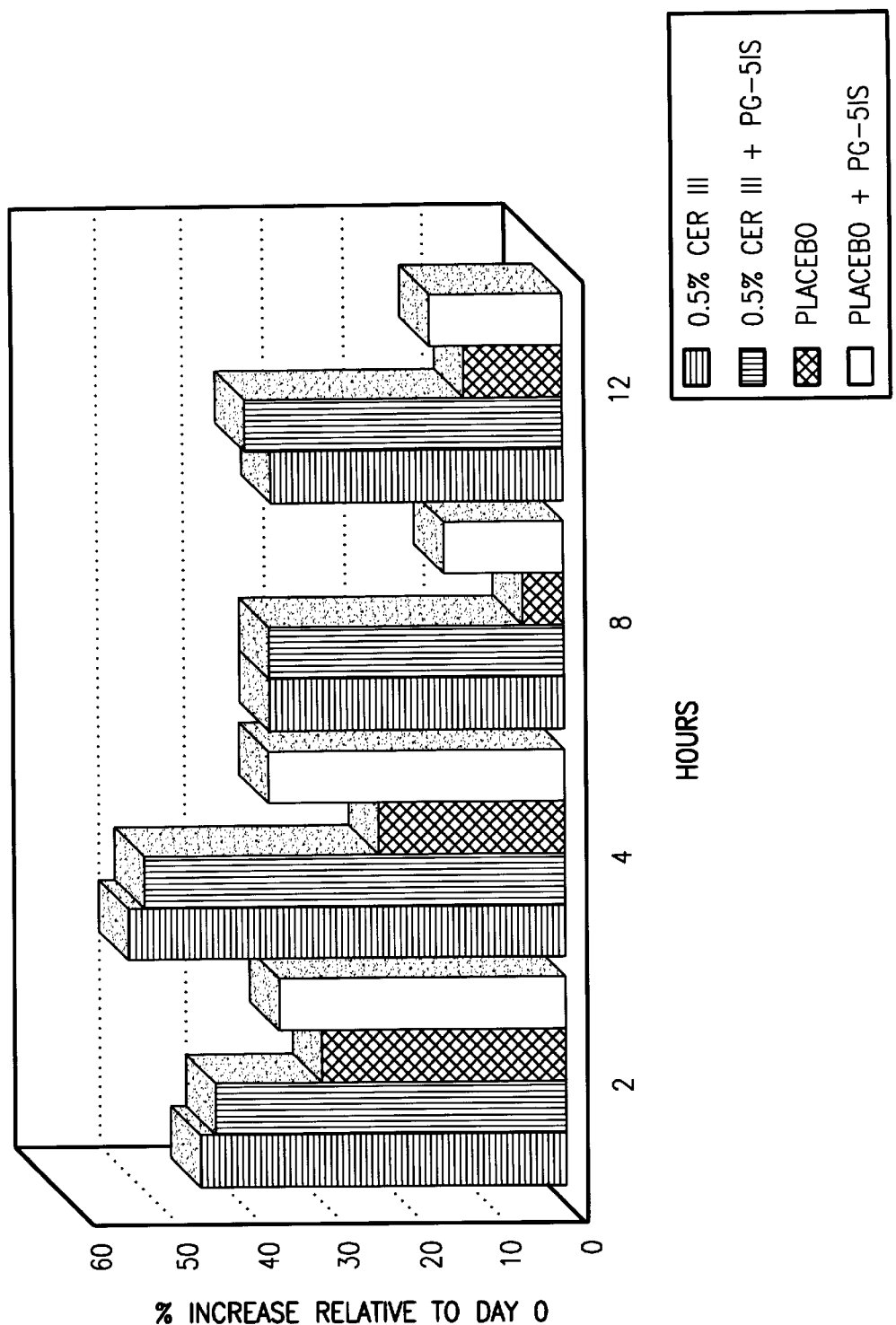
FIG. 6 shows the results of corneometer measurements on healthy skin, after one application of anionic ceramide III formulations.
Figure 7:
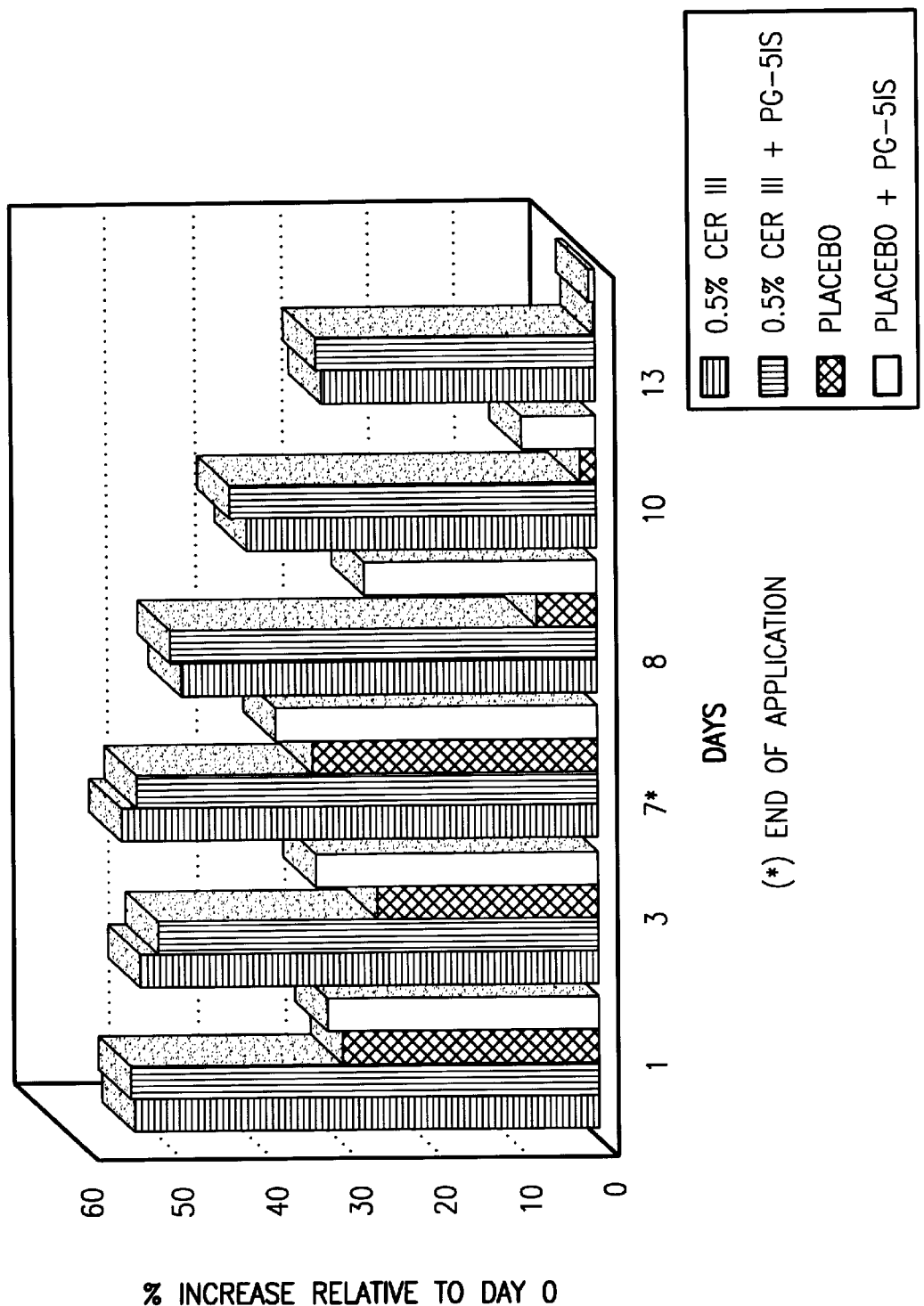
FIG. 7 shows the results of corneometer measurements on healthy skin, during treatment with anionic ceramide III formulations for 7 days and during 6 days after the end of the treatment.

FIGS. 6 and 7 show the results of the effects of Ceramide III after one application (FIG. 6) and after various applications up to day 7 (FIG. 7). The ceramide containing creams (0.5%) gave clear effects compared to placebo. With two daily applications the maximal effect was already achieved after one day and then remained nearly constant throughout the further application period. One, three and six days after the last application the humidity of the skin was still significantly increased compared to placebo and untreated area.

Conclusion

The ceramide containing products gave clear moisturizing effects compared to placebo.

Already after one application, the enhancing effect of ceramides on hydration of the skin could be measured; this increased humidity could be observed until 12 hours after the first application. Also six days after the 7-day treatment, an increased humidity could be measured compared to placebo.

Thus, the effect of ceramide containing preparations in enhancing the properties of the stratum corneum with respect to its water retaining function is proved in this example.

We claim:

1. A composition suitable for topical use comprising a ceramide selected from the group consisting of ceramide III and ceramide VI in an amount from 0.005% to 5% by weight and a skin penetration enhancer selected from the group consisting of Ceteareth-6, Ceteareth-25 and Ceteareth-30 in an amount from 0.1% to 10% by weight of the composition.

2. A composition according to claim 1 wherein the amount of penetration enhancer is in the range from 3 to 5% by weight of the composition.

3. A composition according to claim 1 additionally comprises a polyglyceryl ester.

4. A method for the improvement of the water-retaining capacity of the stratum corneum comprising administering the composition of claim 1 to skin such that the water-retaining capacity of the stratum corneum is enhanced.

5. A method for protection of the skin against irritation comprising administering the composition of claim 1 to the skin.

6. A method for restoration of a damaged skin lipid barrier comprising administering the composition of claim 1 to the skin.

7. The composition according to claim 1 wherein the amount of ceramide is in the range from 0.01% to 2% by weight of composition.

* * * * *